(12) United States Patent
Ohishi

(10) Patent No.: US 9,907,525 B2
(45) Date of Patent: Mar. 6, 2018

(54) X-RAY DIAGNOSTIC APPARATUS AND IMAGE PROCESSING APPARATUS

(71) Applicant: Toshiba Medical Systems Corporation, Otawara-shi (JP)

(72) Inventor: Satoru Ohishi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 167 days.

(21) Appl. No.: 14/953,205

(22) Filed: Nov. 27, 2015

(65) Prior Publication Data

US 2016/0151033 A1 Jun. 2, 2016

(30) Foreign Application Priority Data

Nov. 28, 2014 (JP) ................................ 2014-241735

(51) Int. Cl.
*G06K 9/00* (2006.01)
*A61B 6/00* (2006.01)

(52) U.S. Cl.
CPC .............. *A61B 6/504* (2013.01); *A61B 6/481* (2013.01); *A61B 6/5217* (2013.01)

(58) Field of Classification Search
None
See application file for complete search history.

(56) References Cited

U.S. PATENT DOCUMENTS

| | | | | |
|---|---|---|---|---|
| 2003/0073903 A1* | 4/2003 | Sato | ........................ | A61B 5/416 600/437 |
| 2006/0122492 A1* | 6/2006 | Kucharczyk | ......... | A61B 5/0263 600/420 |
| 2008/0107233 A1* | 5/2008 | Sakaguchi | ........... | A61B 6/4233 378/91 |
| 2008/0273782 A1* | 11/2008 | Ichihara | ............... | A61B 5/0275 382/131 |
| 2013/0077839 A1* | 3/2013 | Horz | ..................... | G06T 11/001 382/130 |
| 2013/0289387 A1* | 10/2013 | Shiodera | ................ | A61B 5/055 600/419 |

FOREIGN PATENT DOCUMENTS

WO  WO 2014133104 A1 *  9/2014 ............. A61B 6/481

* cited by examiner

*Primary Examiner* — Delomia L Gilliard
(74) *Attorney, Agent, or Firm* — Oblon, McClelland, Maier & Neustadt, L.L.P.

(57) ABSTRACT

An X-ray diagnostic apparatus according to an embodiment includes an obtaining unit and a calculating unit. The obtaining unit is configured to, with regard to a plurality of X-ray images that are acquired with time by using a contrast media, obtains first transition information that indicates a time-course transition of a signal intensity of the contrast media in a region of interest that corresponds to a blood vessel and obtains second transition information that indicates a time-course transition of the signal intensity of the contrast media in a region to which the contrast media flows earlier than the region of interest. The calculating unit is configured to analyze the first transition information by using the second transition information to calculate blood flow information on each blood flow in the region of interest.

9 Claims, 9 Drawing Sheets

X-RAY DIAGNOSTIC APPARATUS AND IMAGE PROCESSING APPARATUS

CROSS-REFERENCE TO RELATED APPLICATIONS

This application is based upon and claims the benefit of priority from Japanese Patent Application No. 2014-241735, filed on Nov. 28, 2014; the entire contents of which are incorporated herein by reference.

FIELD

Embodiments described herein relate generally to an X-ray diagnostic apparatus and an image processing apparatus.

BACKGROUND

Conventionally, to observe the vascular structure by conducting angiography imaging, X-ray diagnostic apparatus employ digital subtraction angiography (DSA) imaging. DSA imaging is an imaging method in which an X-ray image (hereinafter, referred to as the "mask image" as appropriate) in a state where the contrast media is not injected and an X-ray image (hereinafter, referred to as the "contrast image" as appropriate) in a state where the contrast media is injected are acquired and subtraction is conducted on the images so that a DSA image is obtained in which only a blood vessel is extracted.

Here, with regard to the region where blood vessels are overlapped on the above-described DSA image, although the blood vessel that is firstly contrast-enhanced due to the contrast media may be observed, it is sometimes difficult to observe the subsequently contrast-enhanced blood vessel. For example, if the overlapped blood vessel is contrast-enhanced before the contrast media is removed from the firstly contrast-enhanced blood vessel, the difficulty arises in distinctively observing the subsequently contrast-enhanced blood vessel and the firstly contrast-enhanced blood vessel.

Therefore, according to conventional technologies, if blood vessels are overlapped on a DSA image, for example, a C-arm is moved to an angle such that the firstly contrast-enhanced blood vessel and the subsequently contrast-enhanced blood vessel are not overlapped, the contrast media is injected again, and a DSA image is obtained. Alternatively, for example, after the catheter is inserted from the firstly contrast-enhanced blood vessel to the periphery side, the contrast media is injected again, and a DSA image is obtained.

DETAILED DESCRIPTION

According to an embodiment, an X-ray diagnostic apparatus includes a processing circuitry. The processing circuitry is configured to, with regard to a plurality of X-ray images that are acquired with time by using a contrast media, obtains first transition information that indicates a time-course transition of a signal intensity of the contrast media in a region of interest that corresponds to a blood vessel and obtains second transition information that indicates a time-course transition of the signal intensity of the contrast media in a region to which the contrast media flows earlier than the region of interest. The processing circuitry is configured to analyze the first transition information by using the second transition information to calculate blood flow information on each blood flow in the region of interest. An X-ray diagnostic apparatus and an image processing apparatus according to an embodiment are explained below with reference to the attached drawings. Here, an explanation is given below of a case where, for example, an X-ray diagnostic apparatus included in a medical information processing system performs an operation; however, there is no limitation on the embodiment.

First Embodiment

Figure 1:
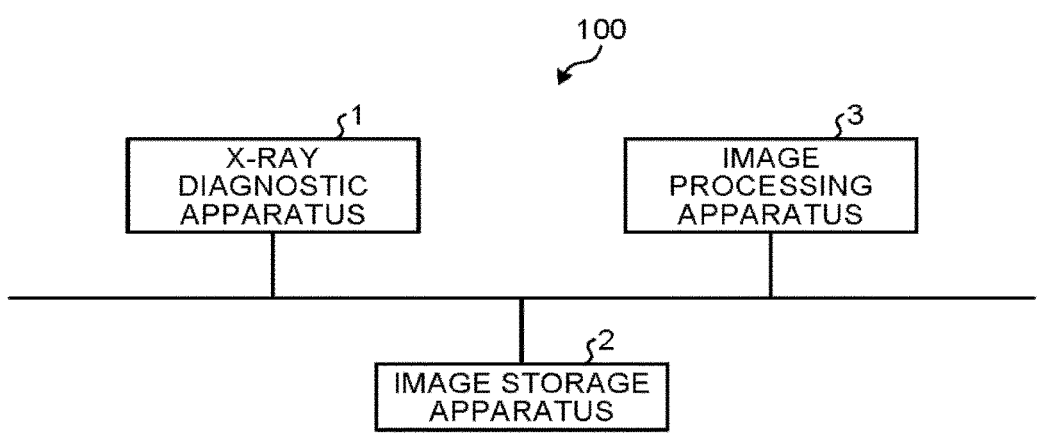
FIG. 1 is a diagram that illustrates an example of the configuration of a medical information processing system according to a first embodiment.

First, an explanation is given of a configuration medical information processing system according to a first embodiment. FIG. 1 is a diagram that illustrates an example of the configuration of a medical information processing system 100 according to the first embodiment. As illustrated in FIG. 1, the medical information processing system 100 according to the first embodiment includes an X-ray diagnostic apparatus 1, an image storage apparatus 2, and an image processing apparatus 3. The apparatus that are illustrated in FIG. 1 are in a state such that they can communicate with one another directly or indirectly via, for example, an in-hospital local area network (LAN) that is installed inside a hospital. For example, a picture archiving and communication system (PACS) is introduced to the medical information processing system 100, and the apparatus transmit and receive X-ray images, or the like, to and from one another in accordance with the Digital Imaging and Communications in Medicine (DICOM) standard.

The image storage apparatus 2 stores X-ray images that are received from the X-ray diagnostic apparatus 1 and various images that are received from the image processing apparatus 3. Here, only the X-ray diagnostic apparatus 1 is illustrated in FIG. 1 as a medical-image diagnostic apparatus; however, there may be a case where an X-ray CT apparatus, MRI apparatus, or the like, is included in the medical information processing system 100. Furthermore, there may be a case where other various information processing apparatus are included in the medical information processing system 100. In such a case, the image storage apparatus 2 may receive images from the various apparatus and store them.

The image processing apparatus 3 performs various types of image processing on medical images that are acquired by the medical-image diagnostic apparatus. For example, the image processing apparatus 3 performs image processing on X-ray images that are acquired from the X-ray diagnostic apparatus 1 or the image storage apparatus 2. Here, the image processing apparatus 3 may perform the same operation as that performed by the X-ray diagnostic apparatus 1 below.

Figure 2:
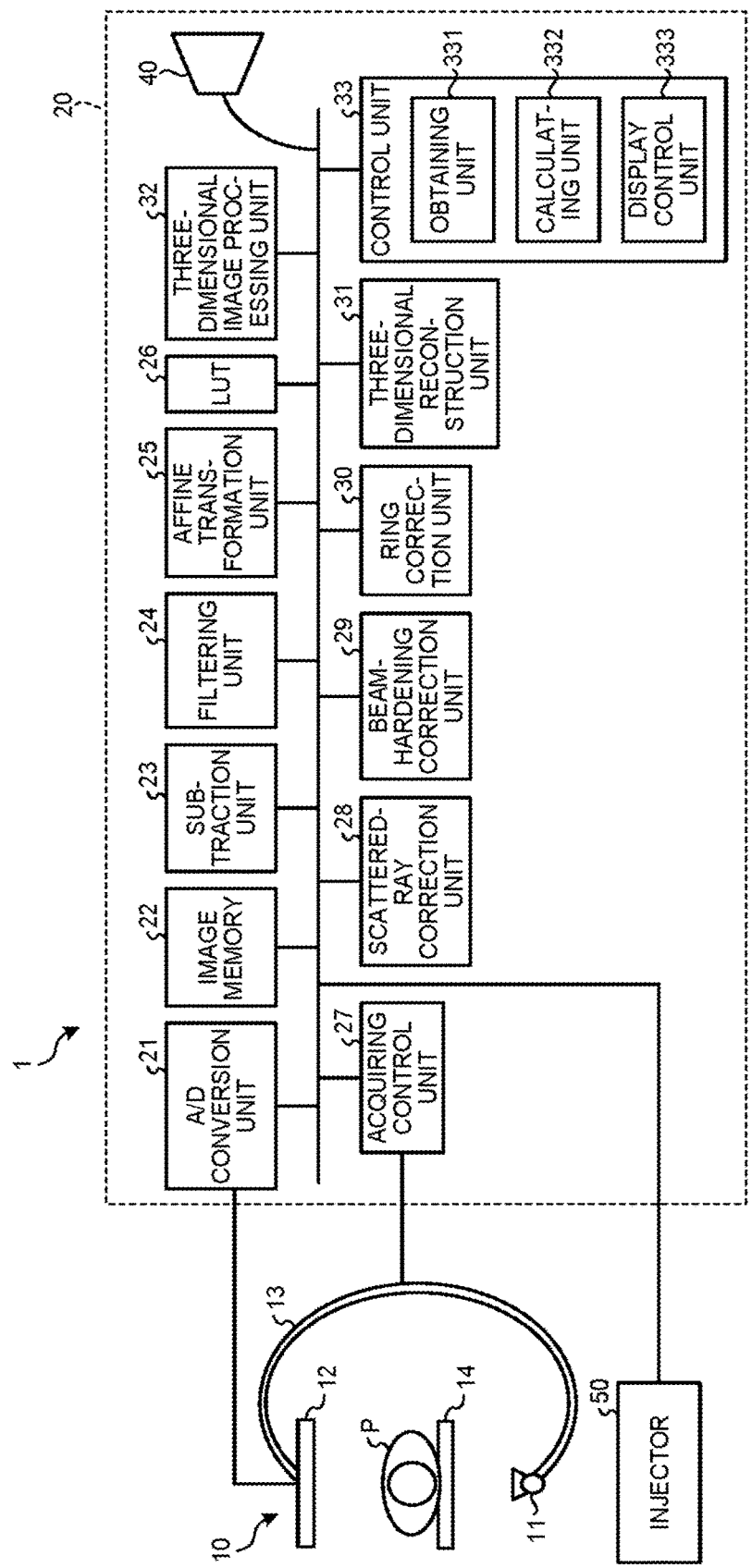
FIG. 2 is a diagram that illustrates an example of the configuration of an X-ray diagnostic apparatus according to the first embodiment.

FIG. 2 is a diagram that illustrates an example of the configuration of the X-ray diagnostic apparatus 1 according to the first embodiment. As illustrated in FIG. 2, the X-ray diagnostic apparatus 1 according to the first embodiment includes an X-ray acquisition mechanism 10 and an image processing apparatus 20. The X-ray acquisition mechanism 10 includes an X-ray tube 11, a detector (flat panel detector (FPD)) 12, a C-arm 13, and a bed 14, and it is connected to air injector 50.

The injector 50 is a device for injecting the contrast media through the catheter that is inserted into a subject P. Here, there may be cases in which injection of tire contrast media from the injector 50 is started in accordance with an injection start command that is received via the image processing apparatus 20 that is described later or in accordance with an injection start command that is directly input to the injector 50 by an operator.

The C-arm 13 supports the X-ray tube 11 and the detector 12, and it is rotated by a motor that is provided on a supporter (not illustrated) at high speed like a propeller around the subject P that lies on the bed 14. Here, the C-arm 13 is supported such that it is rotatable with regard to the XYZ axes that are the three axes that run at right angles, and it is individually rotated by an undepicted driver with respect to each axis.

As illustrated in FIG. 2, the image processing apparatus 20 includes an analog/digital (A/D) conversion unit 21, an image memory 22, a subtraction unit 23, a filtering unit 24, an affirm transformation unit 25, a look up table (LUT) 26, an acquiring control unit 27, a scattered-ray correction unit 28, a beam-hardening correction unit. 29, a ring correction unit 30, a three-dimensional reconstruction unit 31, a three-dimensional image processing unit 32, a control unit 33, and a display 40. Furthermore, although not illustrated, the image processing apparatus 20 includes an input unit, such as a mouse, keyboard, trackball, or pointing device, to receive various operations on the X-ray diagnostic apparatus 1 from an operator.

The display 40 displays various images that are processed by the image processing apparatus 20 and various types of information, such as a graphical user interface (GUI). For example, the display 40 is a cathode ray tube (CRT) monitor or a liquid crystal monitor. The A/D conversion unit 21 is connected to the detector 12, and it converts an analog signal input from the detector 12 into a digital signal and stores the converted digital signal as an X-ray acquisition image in the image memory 22. The image memory 22 stores the X-ray acquisition image (projection data). Furthermore, the image memory 22 stores reconstruction data (volume data) that is reconstructed by the three-dimensional reconstruction unit 31 that is described later and three-dimensional images that are generated by the three-dimensional image processing unit 32. Furthermore, the image memory 22 stores subtraction images that are generated by the subtraction unit 23 that is described later.

The subtraction unit 23 generates subtraction images, such as digital subtraction angiography (DSA) images. For example, the subtraction unit. 23 generates DSA images by using projection data on a mask image and a contrast image that, are stored in the image memory 22 or using volume data.

The filtering unit 24 performs a high-frequency accentuation filtering, or the like. The affine transformation unit 25 enlarges, minifies, moves, or the like, images. The LUT 26 performs a tone conversion. The scattered-ray correction unit 28 performs a scattered-ray correction to remove scattered ray components that are included in a mask image and a contrast image. The beam-hardening correction unit performs a beam hardening correction by using a correction table on the basis of the thickness of soft tissues, the thickness of soft tissues and the thickness of a bone region, or the thickness of soft tissues, the thickness of a bone region and the thickness and density of contrast media. The ring correction unit 30 performs a ring correction to remove ring-shaped artifacts due to the unevenness of gains of the detector 12, or the like.

Under the control of the control unit 33 that is described later, the acquiring control unit 27 controls various operations related to acquiring by the X-ray acquiring mechanism 10. For example, the acquiring control unit 27 controls rotational acquiring for obtaining projection data at a predetermined frame rate while the C-arm 13 is rotated. Furthermore, while the C-arm 13 is controlled so as to rotate, the acquiring control unit 27 controls an undepicted high-voltage generator so as to cause the X-ray tube 11 to generate X-rays continuously or intermittently and controls the detector 12 so as to detect X-rays that are transmitted through the subject P.

The three-dimensional reconstruction unit 31 reconstructs reconstruction data (volume data) from projection data that is obtained during a rotational acquiring by the X-ray acquiring mechanism 10. For example, the three-dimensional reconstruction unit 31 reconstructs volume data from post-subtraction projection data that is stored in the image memory 22 after the subtraction unit performs a subtraction on the mask image and the contrast image. Alternatively, the three-dimensional reconstruction unit 31 reconstructs volume data from the projection data that is stored in the image memory 22 after the A/D conversion unit 21 performs a digital data conversion. Then, the three-dimensional reconstruction unit 31 stores the reconstructed volume data in the image memory 22.

The three-dimensional image processing unit 32 generates a three-dimensional image from volume data that is stored in the image memory 22. For example, the three-dimensional image processing unit 32 generates a volume rendering image or a Multi Planar Reconstruction (MPR) image from volume data. Then, the three-dimensional image processing unit 32 stores the generated three-dimensional image in the image memory 22.

The control unit 33 performs the overall control of the X-ray diagnostic apparatus 1. Specifically, the control unit 33 controls various operations related to acquiring of X-ray images by the X-ray acquiring mechanism 10, analysis of X-ray images, generation of displayed images, presentation of images displayed on the display 40, or the like. For example, the control unit 33 performs a control so as to analyze the transition (time density curve: TDC) of the signal intensity of the contrast media that included in the X-ray image that is acquired by the X-ray acquiring mechanism 10 and to display the analysis result together with the displayed image. Here, as illustrated in FIG. 2, the control unit 33 includes, for example, an obtaining unit 331, a calculating unit 332, and a display control unit 333, and it analyzes the TDC of the contrast media on the X-ray image so as to distinguish the information on overlapped blood vessel in an effective manner.

As described above, in conventional X-ray diagnostic apparatus, for example, if blood vessels (blood flows) are overlapped on a DSA image, the C-arm is moved to an angle such that the firstly contrast-enhanced blood vessel and the subsequently contrast-enhanced blood vessel are not overlapped and then the contrast media is again injected so that the DSA image is obtained, or the catheter is inserted from the firstly contrast-enhanced blood vessel to the periphery side and then the contrast media is again injected so that the DSA image is obtained, whereby blood vessels (blood flows) may be distinguished.

However, for example, in a case where the C-arm is moved to an angle such that blood vessels are not overlapped, if a three-dimensional blood vessel image is not prepared, it sometimes takes time to find the angle at which the firstly contrast-enhanced blood vessel and the subsequently contrast-enhanced blood vessel are not overlapped. Furthermore, even if the C-arm is moved to an angle such that the firstly contrast-enhanced blood vessel and the subsequently contrast-enhanced blood vessel are not overlapped, the blood vessel of interest is sometimes overlapped with a different blood vessel again.

Furthermore, if the catheter is inserted from the firstly contrast-enhanced blood vessel to the periphery side, it is inherently difficult to insert the catheter to the periphery side, or it sometimes takes a considerable time to insert it. As described above, according to the conventional technologies, there may be cases where it takes long time to distinguish between the overlapped blood vessels or it is difficult to distinguish between them. Therefore, with the X-ray diagnostic apparatus 1 according to the present application, the above-described control unit 33 analyses the TDC of the contrast media on an X-ray image (DSA image), whereby the information on the overlapped blood vessels may be distinguished in an effective manner.

Specifically, the obtaining unit 331 obtains first transition information that indicates the time-course transition of the signal intensity of the contrast media in the region of interest that corresponds to a blood vessel on multiple X-ray images that are captured by using the contrast media with the course of time and obtains second transition information that indicates the time-course transition of the signal intensity of the contrast media in the region to which the contrast media flows earlier than the region of interest. For example, the obtaining unit 331 obtains the TDC (first density profile) of the contrast media in the pixel that is included in the region f interest and the TDC (second density profile) of the contrast media in the pixel that corresponds to the blood vessel on the proximal (the heart side) of the region of interest, where the region of interest is the region where blood vessels (blood flows) are overlapped on the DSA image that is generated by the subtraction unit 23.

The calculating unit 332 uses the second transition information to analyze the first transition information, thereby calculating the blood flow information on each blood flow in the region of interest. Specifically, the calculating unit 332 approximates the first transition information and one or more pieces of transition information that are obtained by changing the second transition information by using the factor that is related to the contrast media, thereby calculating the blood flow information on one or more blood flows that are included in the region of interest. Specifically, the calculating unit 332 fits one or more pieces of transition information, which are obtained by deforming the TOG that indicates the second density profile with various modulation factors related to the contrast media, into the TDC that indicates the first density profile. Here, for example, the calculating unit 332 uses, as various modulation factors related to the contrast media, at least one factor among the dilution and spread of the contrast media within a blood vessel, the speed degradation due to the friction of a blood vessel wall, and the reaching delay time.

On the basis of the blood flow information on each blood flow that is calculated by the calculating unit 332, the display control unit 333 causes the display 40 to display at least one of the moving image that indicates the flowing time of the contrast media and the color-phase converted image. Furthermore, the display control unit 333 causes the display 40 to display at least one of the dilution and spread of the contrast media within a blood vessel, the speed degradation due to the friction of a blood vessel wall, the reaching delay time, and the turbulence degree that indicates the turbulence of blood.

Figure 3:
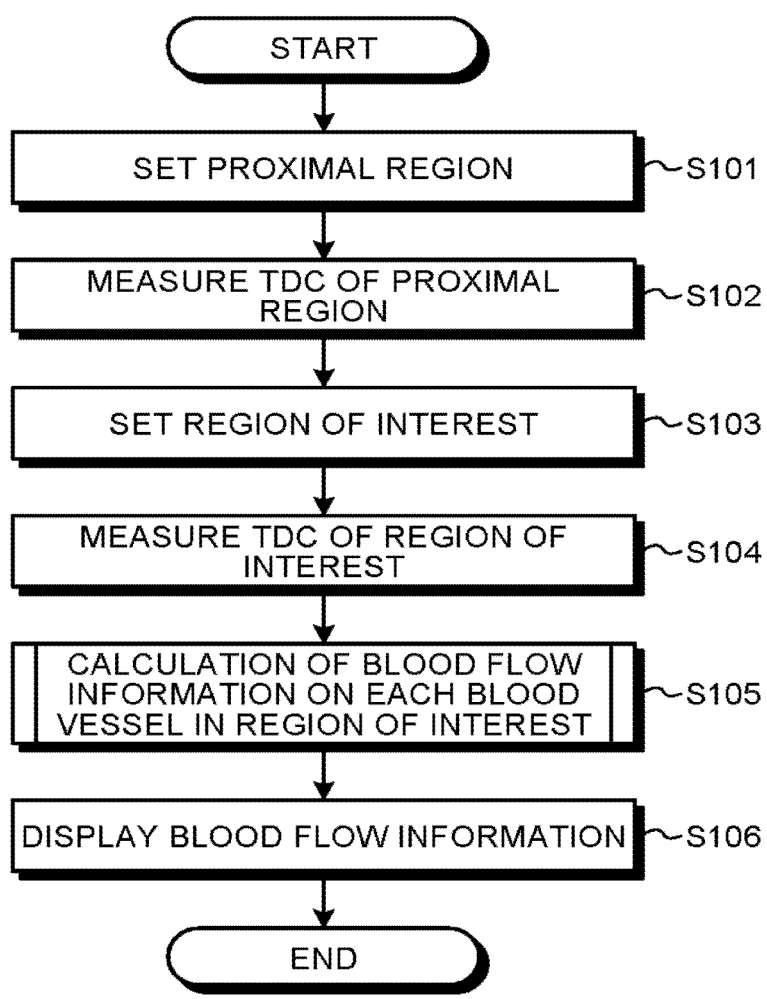
FIG. 3 is a flowchart that illustrates an example of the steps of an operation that is performed by the X-ray diagnostic apparatus according to the first embodiment.
Figure 4:
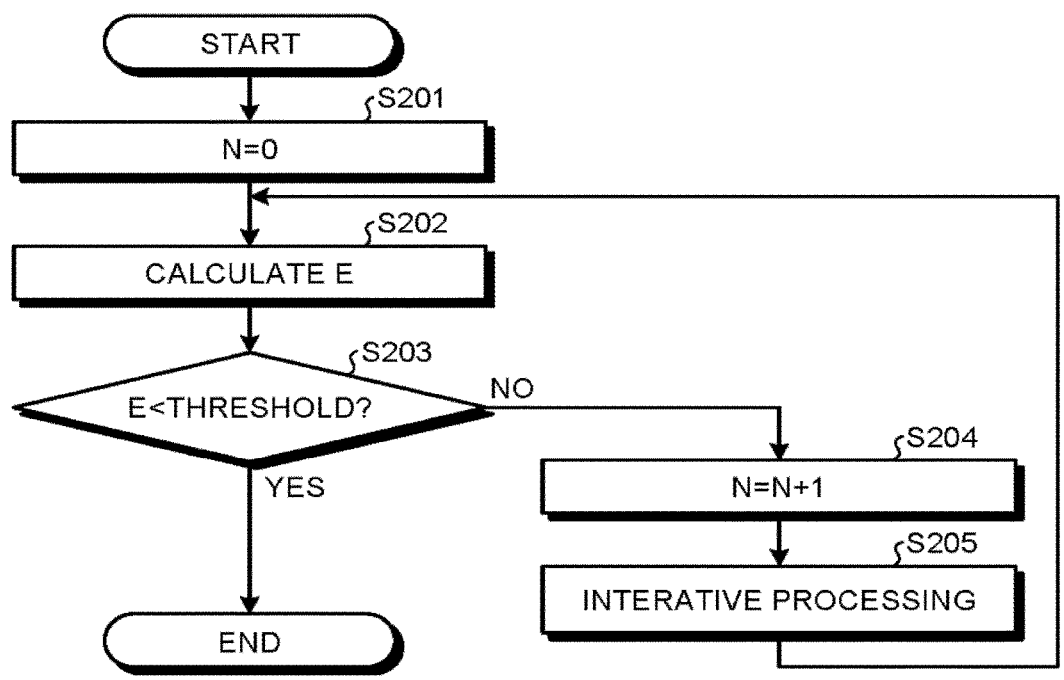
FIG. 4 is a flowchart that illustrates an example of the steps of an operation that is performed by the X-ray diagnostic apparatus according to the first embodiment.

With reference to FIGS. 3 and 4, an explanation is given below of an example of the operation that is performed by the X-ray diagnostic apparatus 1 according to the present embodiment. FIGS. 3 and 4 are flowcharts that illustrate an example of the steps of the operation that is performed by the X-ray diagnostic apparatus 1 according to the first embodiment. Here, FIG. 4 illustrates the details of the operation at Step S105 of FIG. 3. Furthermore, FIG. 3 illustrates an operation after the contrast media is injected into the subject P and a GSA image is generated.

As illustrated in FIG. 2, in the X-ray diagnostic apparatus 1, after the contrast media is injected into the subject P and a subtraction image (e.g., DSA image) is generated from the X-ray moving image that is collected with the course of time, the display control unit 333 causes the display 40 to display the generated DSA image. An operator sees the subtraction image that is displayed on the display 40 and designates the region of interest and the proximal region via the input unit. Here, the region of interest is the region for which the blood flow information needs to be distinguished (for example, the region where blood vessels are overlapped), and the proximal region is the blood vessel region to which the contrast media flows earlier than the region of interest (the region of the blood vessel that is close to the heart than the blood vessel of the region of interest).

Furthermore, the region of interest may be the region that includes a single pixel or multiple pixels. Furthermore, the proximal region may be a single pixel; however, it is preferably the region that includes multiple pixels in order to reduce the effect of noises, and it is preferably the region where a blood vessel runs at right angle to the travelling direction of an X-ray. For example, with regard to a blood vessel that runs at right angle to the travelling direction of an X-ray as much as possible, a line that is perpendicular to the running direction of the blood vessel or a region on the blood vessel is designated as the proximal region.

As described above, after the proximal region is designated, the calculating unit 332 sets the designated position (coordinates) on the subtraction image as the proximal region (Step S101) and measures the TDC of the proximal region (Step S102). For example, the calculating unit 332 measures the TDC of each pixel included in the proximal region by using the time-course subtraction image that is generated from the X-ray moving image and averages the measured TDCs to calculate the TDC of the proximal region. Here, the calculating unit 332 interpolates the discrete value that is obtained from each pixel of the time-course subtraction image by using a linear or high-dimensional function, thereby calculating the continuous TDC "f(t)" of the proximal region.

Furthermore, the calculating unit 332 sets the designated position (coordinates) on the subtraction image as the region of interest (Step S103) and measures the TDC of the region of interest (Step S104). For example, the calculating unit 332 measures the TDC of the pixel in the region of interest by using the time-course subtraction image that is generated from the X-ray moving image and interpolates it by using a linear or high-dimensional function, thereby calculating the continuous TDC of the region of interest.

Then, the calculating unit 332 uses the calculated TDC of the proximal region and the TDC of the region of interest to calculate the blood flow information on each blood vessel (blood flow) in the region of interest (Step S105). Specifically, the calculating unit 332 uses the TDC of the proximal region that has little noise to analyze the TDC that is measured in the region of interest, thereby calculating the blood flow information on each blood flow in the region of interest. Here, the TDC of the proximal region is formed by a single blood flow. Furthermore, the region of interest is the region for which the blood flow information needs be distinguished. Specifically, the calculating unit 332 uses the TDC of the proximal region as a reference and generates the TDC that approximates the TDC of the region of interest by using the reference TDC, thereby analyzing what kind of blood flow forms the TDC of the region of interest.

Figure 5A:
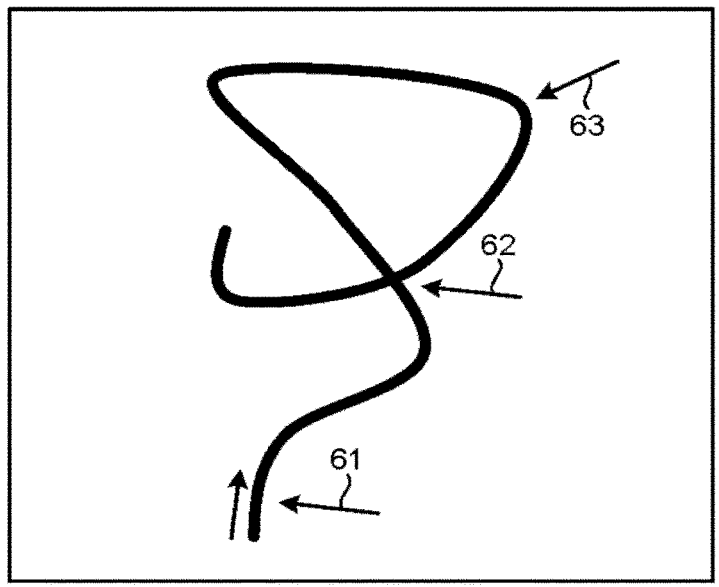
FIGS. 5A to 5D are diagrams that illustrate the relationship between the TDC of a proximal region and the TDC of the region of interest according to the first embodiment.
Figure 5B:
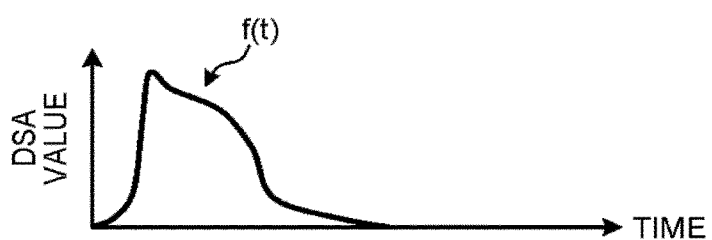
Figure 5C:
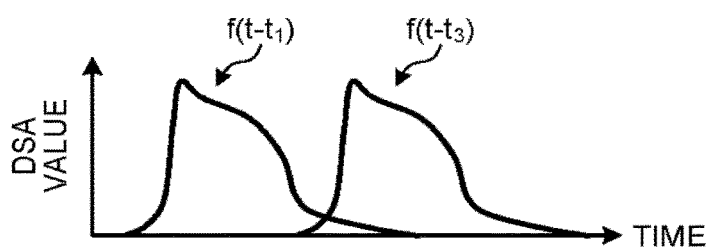
Figure 5D:
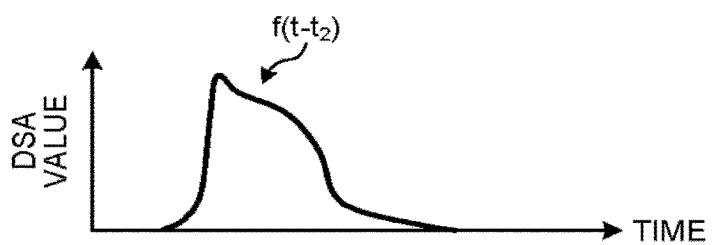
Figure 6A:
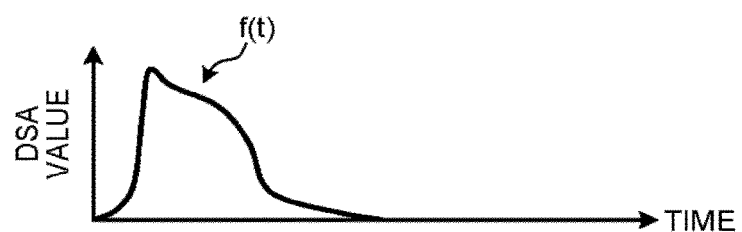
FIGS. 6A to 6C are diagrams that illustrate the relationship between the TDC of the proximal region and the TDC of the region of interest according to the first embodiment.
Figure 6B:
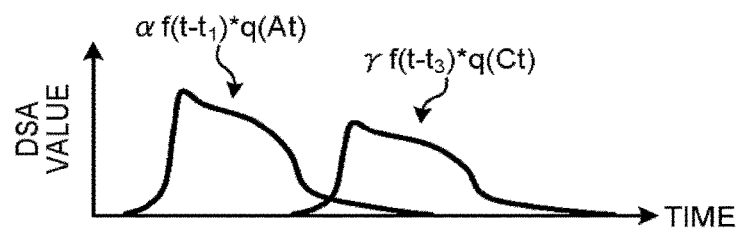
Figure 6C:
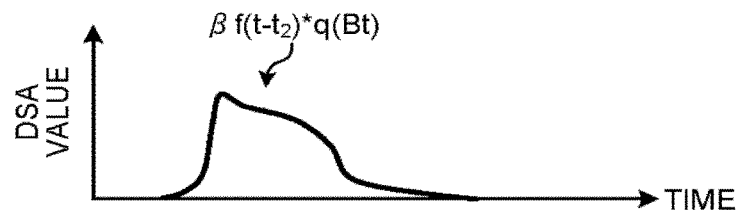

With reference to FIGS. 5A to 5D and FIGS. 6A to 6C, an explanation is given below of the relationship between the TDC of the proximal region and the TDC of the region of interest. FIGS. 5A to 5D and FIGS. 6A to 6C are diagrams that illustrate the relationship between the TDC of the proximal region and the TDC of the region of interest according to the first embodiment. Here, FIGS. 5A to 5D illustrate a simple model that considers ideal flow, and FIGS. 6A to 6C illustrate a complex model that considers various modulation factors. For example, the blood vessel that is the subject to be analyzed runs as illustrated in FIG. 5A, and the blood flows upward as indicated by the arrow in the drawing. Furthermore, with t simple model in a case where the position (region) that is designated by an arrow 61 in the drawing is set as the proximal region, the relationship between the TDC of the proximal region and the TDC of the region of interest is obtained as in, for example, FIGS. 5B to 5D.

For example, the TDC of the proximal region that is designated by the arrow 61 may be represented as TDC "f(t)" whose DSA value rises at time "0" as illustrated in FIG. 5B. Furthermore, in the simple model, the TDC of the region of interest that is designated by arrows 62 and 63 may be represented as the TDC that is shifted from TDC "f(t)" with the course of time. For example, as illustrated in FIG. 5C, the TDC of the region of interest where the blood vessels are overlapped as designated by the arrow 62 may be represented as TDC "f(t−$t_1$)+f(t−$t_3$)" that is formed by TDC "f(t−$t_1$)" based on the contrast media that passes after time "$t_1$" from the proximal region and TDC "f(t−$t_3$)" based on the contrast media that passes after time "$t_3$" from the proximal region.

Furthermore, for example, as illustrated in FIG. 5D, the TDC of the region of interest where no blood vessels are overlapped as designated by the arrow 63 may be represented as TDC "f(t−$t_2$)" based on the contrast media that passes after time "$t_2$" from the proximal region. Specifically, if it is considered with the simple model, the TDC of the region of interest is obtained by simply shifting the reference TDC that is measured in the proximal region in accordance with the time and adding it.

However, if the contrast media actually flows through a blood vessel, the contrast media are affected by various modulation factors, such as dilution due to bloods, spread within a blood vessel, speed degradation due to the friction of a blood vessel wall, or reaching delay; therefore, it cannot be said that the simple model illustrated in FIGS. 5A to 5D reflects the actual status. Therefore, according to the present application, the TDC that approximates the TDC of the region of interest, is generated from the reference TDC by using the complex model that is illustrated in FIGS. 6A to 6C, thereby analyzing what kind of blood flow forms the TDC of the region of interest.

For example, if the complex model is applied to the blood vessel that is illustrated in FIG. 5A, the relationship between the TDC of the proximal region and the TDC of the region of interest are obtained as in FIGS. 6A to 6C. For example, as illustrated in FIG. 6A, the TDC of the proximal region that is designated by the arrow 61 may be represented as TDC "f(t)" whose DSA value rises from the time "O" in the same manner as in FIG. 5B. Furthermore, in the complex model, the TDC of the region of interest that is designated by the arrows 62 and 63 is represented as the TDC that is obtained by deforming the TDC. Shift from TDC "f(t)" is applied with same manner with the simple model. The deformation is mainly composed of two factors, one is weakening/strengthening due to dilution of the contrast media, the thickness change of a blood vessel or the like, and another is spread of the contrast media caused by the Brownian motion, the friction of a blood vessel wall or the like. The weakening/strengthening can be represented by "α" to "γ". The spread is represented by "q(At)" to "q(Ct)".

For example, as illustrated in FIG. 6B, the TDC of the region of interest where the blood vessels are overlapped as designated by the arrow 62 may be represented as TDC "αf(t−$t_1$)*q(At)+γf(t−$t_3$)*q(Ct)" that is formed by using TDC "αf(t−$t_1$)*q(At)" that is obtained by deforming TDC "f(t−$t_1$)" based on the contrast media that passes after the time "$t_1$" from the proximal region with "α" and "g(At)" and by using TDC "γf(t−$t_3$)*q(Ct)" that is obtained by deforming TDC "f(t−$t_3$)" based on the contrast media that passes after the time "$t_3$" from the proximal region with "γ" and "q(Ct)".

Furthermore, for example, as illustrated in FIG. 6C, the TDC of the region of interest where no blood vessels are overlapped as designated by the arrow 63 may be represented as TDC "βf(t−$t_2$)*q(Bt)" that is obtained by deforming TDC "f(t−$t_2$)" based on the contrast media that passes after the time "$t_2$" from the proximal region with "β" and "q(Bt)". The calculating unit 332 according to the first embodiment performs the following operation by using the above-described complex model, thereby calculating the blood flow information on each blood vessel in the region of interest.

For example, the calculating unit 332 uses the following Equation (1) to calculate the TDC of the region of interest that is represented by using the TDC "f(t)" of the proximal region. Here, "g(t)" in Equation (1) represents the TDC of the region of interest, "$A_i$ (here, $A_0$=0)" represents the factor for adjusting dilution of the contrast media, the thickness of a blood vessel, beam hardening effect, and the angle is formed between the blood vessel and the travelling direction of an X-ray, and "$\Delta t_1$" represents speed degradation due to the friction of a blood vessel wall and the reaching delay time. It is preferable to apply beam hardening correction for the subtraction image at the beam-hardening correction unit 29 between Step S101 and S102. Furthermore, "q(t)" in Equation (1) represents spread function, "*" represents a convolution operator, and "N" represents the number of blood vessel (the number 2 blood flows).

$$g(t) = \sum_{i=0}^{N} A_i q(t) * f(t - \Delta t_i) \quad (1)$$

For example, the calculating unit 332 calculates the TDC that is obtained by deforming "f(t)" with various modulation factors with respect to each overlapped blood vessel (blood flow) as represented by Equation (1) and adds the calculated TDCs to calculate TDC "g(t)" of the region of interest. Here, the spread "q(t)" in Equation (1) is calculated by using the following Equation (2). Here, "$\sigma_i$" in Equation (2) represents a spread coefficient.

$$q(t) = \frac{1}{\sqrt{2\pi\sigma_i^2}} \exp\left(\frac{t^2}{2\sigma_i^2}\right) \quad (2)$$

For example, the calculating unit 332 uses the following Equation (3) to calculate a deviation between the TDC of the region of interest that is calculated by using Equation (1) and the TDC of the region of interest that is actually measured and conduct, iterative processing to change the number of blood vessels (the number of blood flows) and e modulation factor so that the calculated deviation is equal to or less than a predetermined threshold.

$$E = \|g(t) - g_0(t)\|^2 \quad (3)$$

Figure 7:
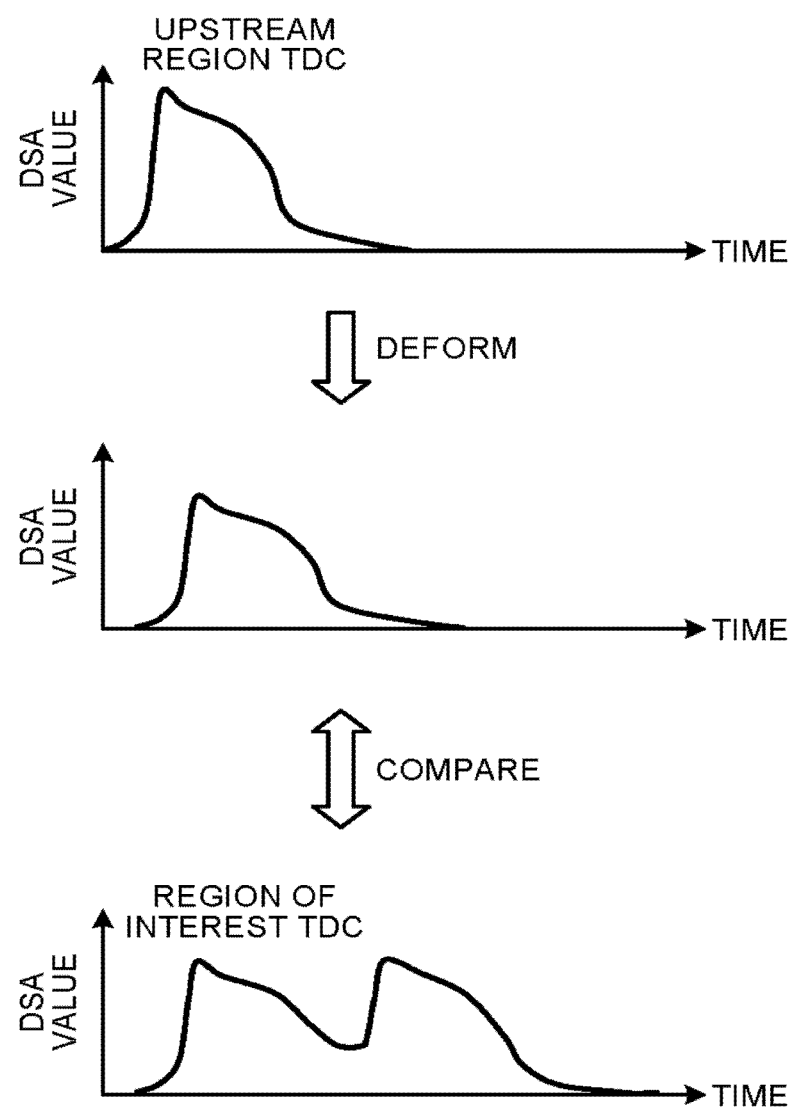
FIG. 7 is a diagram that illustrates an example of the operation that is performed by a calculating unit according to the first embodiment.

For example, as represented by Equation (3), the calculating unit 332 calculates difference "E" between the calculated TDC "g(t)" of the region of interest and the measured TDC "$g_0(t)$" of the region of interest and compares the calculated "E" with the predetermined threshold. An example of the operation that is performed by the calculating unit 332 is explained below with reference to FIG. 4 and FIG. 7. Here, FIG. 7 is a diagram that illustrates an example of the operation that is performed by the calculating unit 332 according to the first embodiment. For example, as illustrated in FIG. 4, the calculating unit 332 first applies "N=0" where no blood vessels run (there are no blood flows) in the region of interest (Step S201) and calculates the deviation "E" (Step S202).

Then, the calculating unit 332 determines whether the calculated deviation "E" is less than the threshold (Step S203). Here, if "E" is less than the threshold (Yes at Step S203), the calculating unit 332 terminates the operation. That is, no blood vessels run (there are no blood flows) in the region of interest that is designated by an operator.

Conversely, at Step S203, if "E" is equal to or more than the threshold (No at Step S203), the calculating unit 332 sets "N=N+1" (Step S204) and conducts an iterative processing (Step S203). For example, as illustrated in FIG. 7, the calculating unit 332 deforms the TDC of the proximal region by using various modulation factors and compares it as the TEC that is measured in the region of interest. Here, the calculating unit 332 adjusts the factors "$A_i$", "$\Delta t_i$", and "$\sigma_i$" so that the TDC of the proximal region approximates the measured TDC, calculates "E", and then determines whether "E" is less than the threshold again (Step S203).

Here, if "E" is not less than the threshold, the calculating unit 33 increments the number of blood vessels (the number of blood flows) by one and performs the same operation as for "N=N+1". In this way, the calculating unit 332 continues the operation by incrementing the number of blood vessels (the number of blood flows) by one until the deviation "E" becomes less than the predetermined threshold. Furthermore, the maximum value is previously set for the number of "N" and, if not "E<the threshold" although "N=the maximum value", a result with the minimum "E" may be obtained from the previous results. Thus, the blood flow information may be calculated even if the maximum value is improperly set, if the blood flow is significantly changed due to the turbulence of blood, if there are a lot of noises, or the like.

Furthermore, in the above-described Equation (3) although spread is represented by using an ideal equation, it sometimes actually deviates from the ideal equation due to the effect of friction of a blood vessel wall, or the like. Therefore, in such a case, the calculating unit 332 compares the TDC of the proximal region with the TDC of a distal region to which the contrast media flows later than the region of interest and where no blood vessels are overlapped, calculates the spread function "q(t)" on the basis of changes in the two TDCs, and performs the above-described operation by using the calculated spread function "g(t)".

As described above, the calculating unit 332 conducts the iterative processing to change the number of blood vessels (the number of blood flows) and each modulation factor so that the calculated deviation becomes equal to or less than the predetermined threshold, thereby calculating the blood flow information on each blood flow (blood vessel) in the region of interest. That is, the calculating unit 332 uses Equation (1) to (3) so as to estimate each TEC that is formed by a blood flow that is included in the region of interest and, for example, calculate various types of blood flow information by using the estimated TDC.

Figure 8:
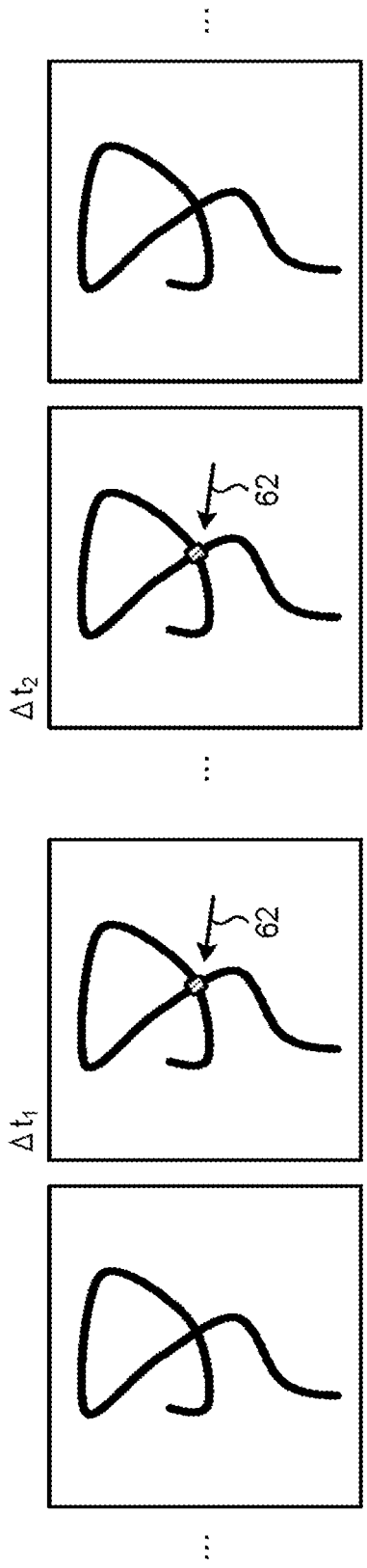
FIG. 8 is a diagram that illustrates an example of the moving image that is displayed by a display control unit according to the first embodiment.

With reference back to FIG. 3, after the blood flow information is calculated Step S105, the display control unit 333 displays the blood flow information (Step S106). For example, the display control unit 333 selects the optimally contrast-enhanced frame of each overlapped blood vessel in the region of interest and displays the region of interest in the selected frame in synchronized with the contrast-enhancing timing. FIG. 8 is a diagram that illustrates an example of the moving image that is displayed by the display control unit 333 according to the first embodiment. Here, the frames that are continuously displayed as a moving image are arranged horizontally in the illustration of FIG. 8.

As a result of analysis by the calculating unit 332, for example, if the overlapped blood vessels in the region of interest that is designated by the arrow 62 are optimally contrast-enhanced at "$\Delta t_1$" and "$\Delta t_2$" (for example, the DSA value reaches a peak), the display control unit 333 displays the moving image in which the region of interest in the frames at "$\Delta t_1$" and "$\Delta t_2$" are highlighted, as illustrated in FIG. 8. For example, the display control unit 333 displays the pixel of the region of interest in an easily viewable color (e.g., red). Here, the brightness of red at that time may be changed in accordance with the intensity of "$A_i$".

Furthermore, in the case of the above-described example, as highlight is displayed only during a specific time, it is difficult to be recognized. Therefore, it is possible provide ranges to the frame that is highlighted so that recognition facilitated. For example, the display control unit 333 may display the region of interest in the frames between "t=Δt$_1$−Δ/2" and "t=Δt$_1$+Δ/2" in red in addition to displaying it in red only at "t=Δt$_1$". Furthermore, for example, the display control unit 333 may conduct shading on the frames between "t=Δt$_1$−Δ/2" and "t=Δt$_1$+Δ/2" so that it is displayed with the maximal brightness only at "t−Δt$_1$", it is displayed with a gradually increasing brightness at between "t−Δt$_1$−Δ/2" and "t=Δt$_1$", and it is displayed with a gradually decreasing brightness at between "t−Δt$_1$" and "t−Δt$_1$+Δ/2". Furthermore, for example, the display control unit 333 may display it in red only at "t=Δt$_1$" between "t=Δt$_1$−Δ/2" and "t=Δt$_1$+Δ/2" and display it by gradually changing from blue to red at between "t−Δt$_1$−Δ/2" and "t=Δt$_1$" and gradually changing from red to blue at between "t=Δt$_1$−Δ/2" and "t−Δt$_1$+Δ/2".

The operation of the X-ray diagnostic apparatus 1 according the first embodiment has been described above. However, this is not a limitation on the embodiment and, for example, the above described Equation (3) may be deformed into various equations. For example, Equation (3) may be deformed into the following Equation (4) so that the element (the TDC of each blood flow) "A$_i$g(t)*f(t−Δt$_i$)" included in the TDC "g(t)" of the region of interest is prevented from being a set of elements that hardly indicate blood flows. Here, the profile "g(t)" in Equation (4) is represented as a profile by obtaining the TDC of the region of interest that is calculated by the calculating unit 332 as a set of pixels, and the profile "g$_0$(t)" is represented as a profile by obtaining the measured TDC of the region of interest as a set of pixels. Furthermore, the scalar "N" in Equation (4) is represented as a scalar by obtaining the maximum number of blood vessels as a set of pixels.

$$E=\|\vec{g}(t)-\vec{g}_0(t)\|^2+v\vec{N}\|^2 \quad (4)$$

Furthermore, in the above-described embodiment, an explanation is given of a case where the region of interest is a single pixel. However, this is not a limitation on the embodiment, and there may be a case where the region of interest includes multiple pixels. In such a case, the above-described operation is performed on each pixel. Here, if the region of interest includes multiple pixels, the difference with an adjacent pixel may be used.

In the above case, for example, the calculating unit 332 deforms Equation (3) into the following Equation (5) and makes an analysis. Here, the term MIN in Equation (5) represents, among the differences between the TDC of an arbitrary pixel and the TDC of each of the 8 pixels that are adjacent to the pixel, the one with the smallest difference.

$$E=\|\vec{g}(t)-\vec{g}_0(t)\|^2+\|MIN(\Delta\vec{g}(t))\|^2 \quad (5)$$

It is considered that, as the blood vessel is continuous, the adjacent pixels include the pixel that indicates substantially the same TDC. Therefore, the calculating unit 332 performs an iterative processing so as to minimize the difference with the TDC of the adjacent pixel, as represented by Equation (5). Furthermore, if the iterative processing is performed by using the above-described Equation (4) and Equation (5), a particular algorithm, such as "simulated annealing" or "genetic algorithm" is used; therefore, in order to prevent the use of such a complex algorithm, the threshold of "A$_i$" may be set more simply so that it is prevented from being equal to or less than the threshold.

Modified Example 1

Figure 9:
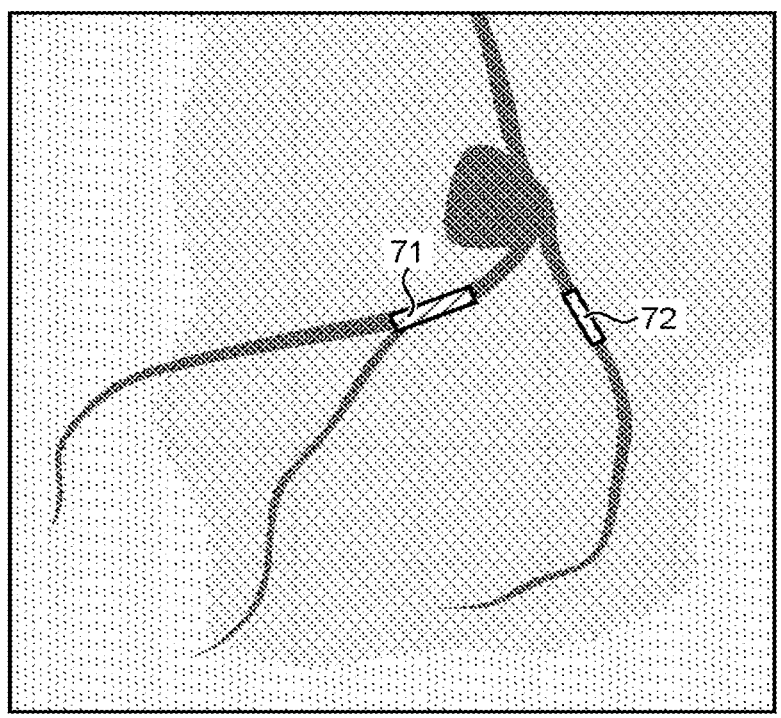
FIG. 9 is a diagram that illustrates an example of the image that is displayed by the display control unit according to a modified example.

In the above-described embodiment, an explanation is given of a case where the flowing time of the contrast media is displayed as the display information. However, this is not a limitation on the embodiment and, for example, there may be a case where at least one of the dilution and spread of the contrast media within a blood vessel, the speed degradation due to the friction of a blood vessel wall, the reaching delay time, and the turbulence degree that indicates the turbulence of blood is displayed in the display 40. FIG. 9 is a diagram that illustrates an example of the image that is displayed by the display control unit 333 according to a modified example. Furthermore, FIG. 9 illustrates a case where, among the above-described factors, the spread (spread coefficient) is displayed.

For example, as illustrated in FIG. 9, the display control unit 333 displays, on the image, the information on the spread coefficient with regard to blood vessels (a blood vessel portion 71 and a blood vessel portion 72) at the positions that correspond to predetermined periods (e.g., Δt=t$_1$ to t$_2$) on the moving image. For example, the display control unit performs a control such that, the spread coefficient becomes higher, the display becomes more red and, as the spread coefficient becomes lower, the display becomes more blue. Furthermore, the colors may be optionally set. Thus, it is possible to instantly recognize the region with a high spread coefficient. Furthermore, the cause of changes in the spread coefficient includes, for example, spread, infarction, or turbulence.

Furthermore, the display control unit 333 may display the turbulence degree on an image as a the case with the above-described spread coefficient. For example, the display control unit 333 assigns a color phase in accordance with the value of the turbulence degree and displays the image in which the blood vessel is colored on the basis of the turbulence degree within the blood vessel. Here, the above-described turbulence degree is calculated by the calculating unit 333. Specifically, the calculating unit 332 calculates, as the turbulence degree that indicates the turbulence of blood, the deviation between the first transition information and one or more pieces of transition information that are obtained when the blood flow information is calculated on each blood flow that is included in the region of interest. That is, the calculating unit 332 sets, as the turbulence degree, the value of the deviation "E" that is equal to or less than the threshold by ng Equation (3), Equation (4), and Equation (5). For example, the position of which the turbulence degree needs to be calculated is set ac the region of interest with regard to the blood vessel in the subtraction image, whereby the image that indicates the turbulence degree of each position may be observed.

If each of the above-described factors is displayed on the image, a GUI such as a radio button may be displayed on the display 40 so that the displayed factor is optionally switched. Furthermore, the range (e.g., the above-described period "Δt=t$_1$ to t$_2$") that is displayed with regard to each factor, or the like, may be optionally set in accordance with a request from an operator.

As described above, according to the first embodiment, with regard to multiple X-ray images that are captured with the course of time by using the contrast media, the obtaining unit 331 obtains the first transition information that indicates the time-course transition of the signal intensity of the contrast media in the region of interest that corresponds to a blood vessel and obtains the second transition information that indicates the time-course transition of the signal intensity of the contrast media in the region to which the contrast media flows earlier than the region of interest. The calculating unit 332 analyzes the first transition information by using the second transition information, thereby calculating the blood flow information on each blood flow in the region of interest. Therefore, the X-ray diagnostic apparatus 1 according to the first embodiment makes it possible to distinguish the information on the overlapped blood flow in the region of interest in an effective manner. As a result, the X-ray diagnostic apparatus 1 according to the first embodiment may shorten the time of various surgeries.

Furthermore, according to the first embodiment, the calculating unit 332 calculates the first transition information with one or more pieces of transition information that are obtained by changing the second transition information by using a modulation factor that is related to the contrast media in the region of interest. Therefore, the X-ray diagnostic apparatus 1 according to the first embodiment makes it possible to distinguish the information on a blood flow in consideration of the contrast media that actually flows through a blood vessel.

Furthermore, according to the first embodiment, the calculating unit 332 calculates the blood flow information on each blood flow by using, as the modulation factor that is related to the contrast media, at least one of the dilution and spread of the contrast media within a blood vessel, the speed degradation due to the friction of a blood vessel wall, and the reaching delay time. Therefore, the X-ray diagnostic apparatus 1 according to the first embodiment may perform higher-accuracy processing.

Furthermore, according to the first embodiment, the calculating unit 332 changes the second transition information so as to minimize the difference with the time-course transition of the signal intensity of the contrast media in the region that is adjacent to the region of interest. Therefore, when the X-ray diagnostic apparatus 1 according to the first embodiment analyzes multiple pixels, it may perform higher-accuracy processing.

Furthermore, according to the first embodiment, the calculating unit 332 implements a iterative processing method to change the number of blood flows that are overlapped in the region of interest such that the difference between the first transition information and one or more pieces of transition information that are obtained by changing the second transition information becomes equal to or less than a predetermined threshold, thereby calculating the number of blood flows that are overlapped in the region of interest and the blood flow information on each blood flow that is included in the first transition information. Therefore, the X-ray diagnostic apparatus 1 according to the first embodiment makes it possible to distinguish the information on each blood vessel (blood flow) in an effective manner even if multiple blood vessels (blood flows) are overlapped.

Furthermore, according to the first embodiment, the calculating unit 332 calculates, as the turbulence degree that indicates the turbulence of blood, the deviation between the first transition information and one or more pieces of transition information that are obtained when the blood flow information calculated on each blood flow that is included in the region of interest. Therefore, the X-ray diagnostic apparatus 1 according to the first embodiment allows display of the information that indicates the state within a blood vessel.

Furthermore, according to the first embodiment, the display control unit 333 causes the display 40 to display at least any one of the moving image that indicates the flowing time of the contrast media and the color-phase converted image on the basis of the blood flow information on each blood flow that is calculated by the calculating unit 332. Furthermore, the display control unit 333 causes the display 40 to display at least one of the dilution and spread of the contrast media within a blood vessel, the speed degradation due to the friction of a blood vessel wall, the reaching delay time, and the turbulence degree that indicates the turbulence of blood. Therefore, the X-ray diagnostic apparatus 1 according to the first embodiment allows display of various types of blood flow information to an operator.

Second Embodiment

Although the first embodiment has been described above, various different embodiments may be implemented other than the above-described first, embodiment.

In the above-described first embodiment, an explanation is given of a case where the X-ray diagnostic apparatus 1 performs each operation. However, this is not a limitation on the embodiment, and there may be a case where the image processing apparatus 3 performs it. That is, a control unit of the image processing apparatus 3 includes the obtaining unit 331, the calculating unit 332, and the display control unit 333 that are described above, and each of the unit performs the same operation as the above-described operation.

Furthermore, components of each apparatus that is illustrated in the first embodiment are functionally conceptual and do not necessarily need to be physically configured as illustrated in the drawings. Specifically, specific forms of separation and combination of each apparatus are not limited to those depicted in the drawings, and a configuration may be such that all or some of them are functionally or physically separated or combined in an arbitrary unit depending on various types of loads, usage, or the like. Moreover, all or any of various processing functions performed by each apparatus may be implemented by a CPU and a program that is analyzed and executed by the CPU or may be implemented as wired logic hardware.

Furthermore, the control method that is described in the first embodiment may be implemented when a prepared control program is executed by a computer, such as a personal computer or workstation. The control program may be distributed via a network, such as the Internet. Furthermore, the control program is recorded in a recording medium readable by a computer, such as a hard disk, flexible disk (FD), CD-ROM, MO, or DVD, and it may be executed when it is read from the recording medium by the computer.

As described above, according to the first embodiment, and the second embodiment, the X-ray diagnostic apparatus and the image processing apparatus of the present embodiment make it possible to distinguish the information on overlapped blood flows in an effective manner.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising a processing circuitry configured to with regard to a plurality of X-ray images that are acquired with time by using a contrast media, obtains first transition information that indicates a time-course transition of a signal intensity of the contrast media in a region of interest that corresponds to a blood vessel and obtains second transition information that indicates a time-course transition of the signal intensity of the contrast media in a region to which the contrast media flows earlier than the region of interest, and analyze the first transition information by using the second transition information to separate blood flow information in the region of interest into a plurality of pieces of blood flow information corresponding to a plurality of blood flows.

2. The X-ray diagnostic apparatus according to claim 1, wherein the processing circuitry is configured to approximate the first transition information with one or more pieces of transition information that are obtained by changing the second transition information by using a factor that is related to the contrast media, thereby calculating blood flow information on one or more blood flows that are included in the region of interest.

3. The X-ray diagnostic apparatus according to claim 2, wherein the processing circuitry is configured to calculate the blood flow information on each blood flow by using, the factor that is related to the contrast media, at least one of dilution and spread of the contrast media within a blood vessel, speed degradation due to a friction of a blood vessel wall, and a reaching delay time.

4. The X-ray diagnostic apparatus according to claim 2, wherein the processing circuitry is configured to change the second transition information so as to minimize a difference with a time-course transition of the signal intensity of the contrast media in a region that is adjacent to the region of interest.

5. The X-ray diagnostic apparatus according to claim 2, wherein the processing circuitry is configured to implement a iterative processing method to change a number of blood flows that are overlapped in the region of interest such that a difference between the first transition information and combination of one or more pieces of transition information that are obtained by changing the second transition information becomes equal to or less than a predetermined threshold, thereby calculating a number of blood flows that are overlapped in the region of interest and blood flow information on each blood flow that is included in the first transition information.

6. The X-ray diagnostic apparatus according to claim 2, wherein the processing circuitry is configured to calculate, as a turbulence degree that indicates turbulence of blood, a deviation between the first transition information and combination of the one or more pieces of transition information that are obtained when blood flow information is calculated on each blood flow that is included in the region of interest.

7. The X-ray diagnostic apparatus according to claim 1, wherein the processing circuitry is further configured to cause a display to display at least any one of a moving image that indicates a flowing time of the contrast media and a color-phase converted image in accordance with the calculated blood flow information on each blood flow.

8. The X-ray diagnostic apparatus according to claim 7, wherein the processing circuitry is configured to cause the display to display at least one of dilution and spread of the contrast media within a blood vessel, a speed degradation due to a friction of a blood vessel wall, a reaching delay time, and a turbulence degree that indicates turbulence of blood.

9. An image processing apparatus comprising a processing circuitry configured to with regard to a plurality of X-ray images that are acquired with time by using a contrast media, obtains first transition information that indicates a time-course transition of a signal intensity of the contrast media in a region of interest that corresponds to a blood vessel and obtains second transition information that indicates a time-course transition of the signal intensity of the contrast media in a region to which the contrast media flows earlier than the region of interest, and analyze the first transition information by using the second transition information to separate blood flow information in the region of interest into a plurality of pieces of blood flow information corresponding to a plurality of blood flows.

\* \* \* \* \*